US008682421B2

(12) United States Patent
Riftine

(10) Patent No.: US 8,682,421 B2
(45) Date of Patent: Mar. 25, 2014

(54) FITNESS SCORE ASSESSMENT BASED ON HEART RATE VARIABILITY ANALYSIS DURING ORTHOSTATIC INTERVENTION

(75) Inventor: Alexander Riftine, Brooklyn, NY (US)

(73) Assignee: Fitnesscore, Inc., Ronkonkoma, NY (US)

( * ) Notice: Subject to any disclaimer, the term of this patent is extended or adjusted under 35 U.S.C. 154(b) by 294 days.

(21) Appl. No.: 12/916,559

(22) Filed: Oct. 31, 2010

(65) Prior Publication Data

US 2012/0108916 A1    May 3, 2012

(51) Int. Cl.
*A61B 5/024* (2006.01)
*A61B 5/04* (2006.01)
*A61B 5/00* (2006.01)

(52) U.S. Cl.
CPC ........... *A61B 5/0006* (2013.01); *A61B 5/02405* (2013.01); *A61B 5/02438* (2013.01); *A61B 5/486* (2013.01); *A61B 2560/0468* (2013.01)
USPC ........................................................ 600/515

(58) Field of Classification Search
USPC .......................... 600/508, 509, 515, 519, 520
See application file for complete search history.

(56) References Cited

U.S. PATENT DOCUMENTS 6,212,427 B1 * 4/2001 Hoover ......................... 600/515
6,572,511 B1 * 6/2003 Volpe ............................... 482/4

* cited by examiner

*Primary Examiner* — Carl H Layno
*Assistant Examiner* — Jon Eric C Morales
(74) *Attorney, Agent, or Firm* — Gary J. Gershik; Cooper & Dunham LLP

(57) ABSTRACT

This invention relates to fitness monitors and the like. This invention is more particularly directed to a device and a method for facilitating quantitative evaluation of level of physical fitness (fitness score) including a PC or handheld, or watch type electronic device having input and output means based on formulas for calculating level of physical fitness through heart rate variability analysis during orthostatic intervention by assessing two main parameters, such as level of adaptation reserve and wellness level.

15 Claims, 9 Drawing Sheets

Illustration of Optimum and Non- Optimum function of Heart Rate Variability regulation mechanisms during some physical or physiological intervention.

Figure 2:
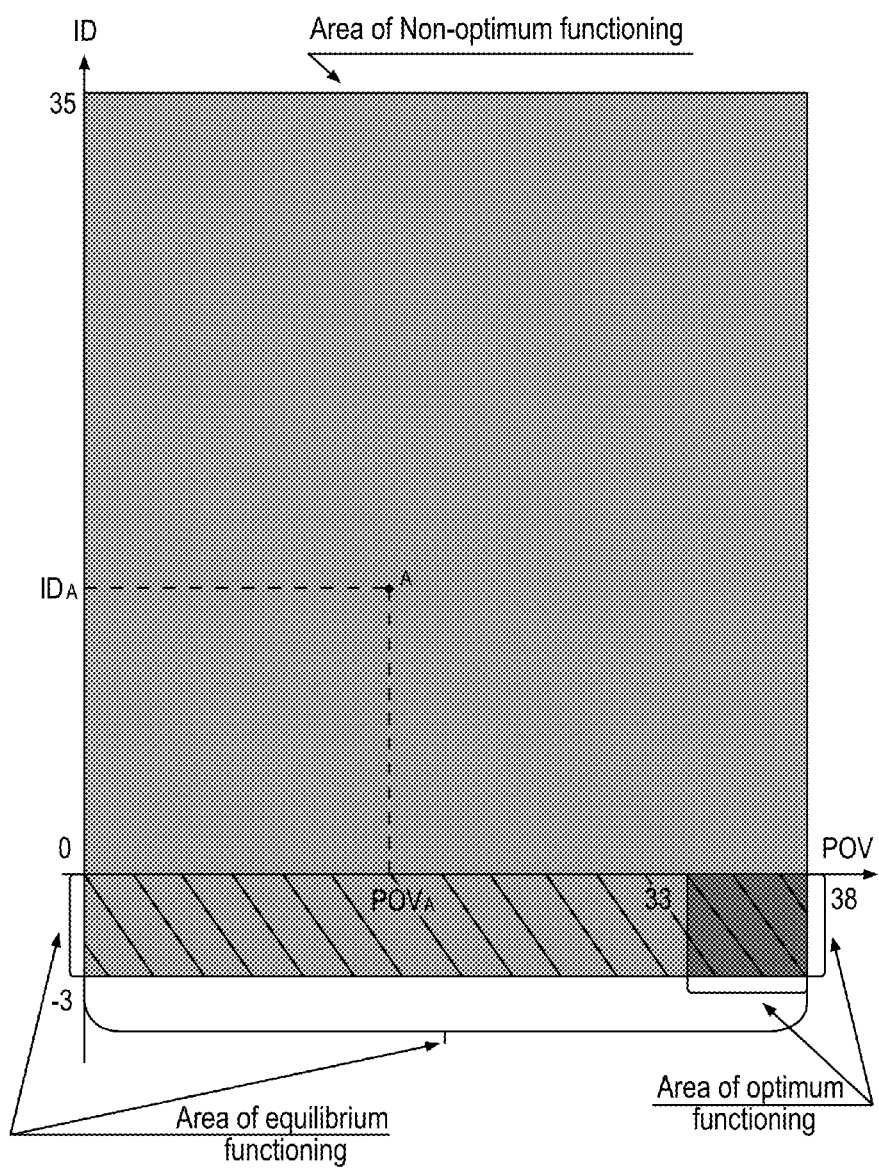

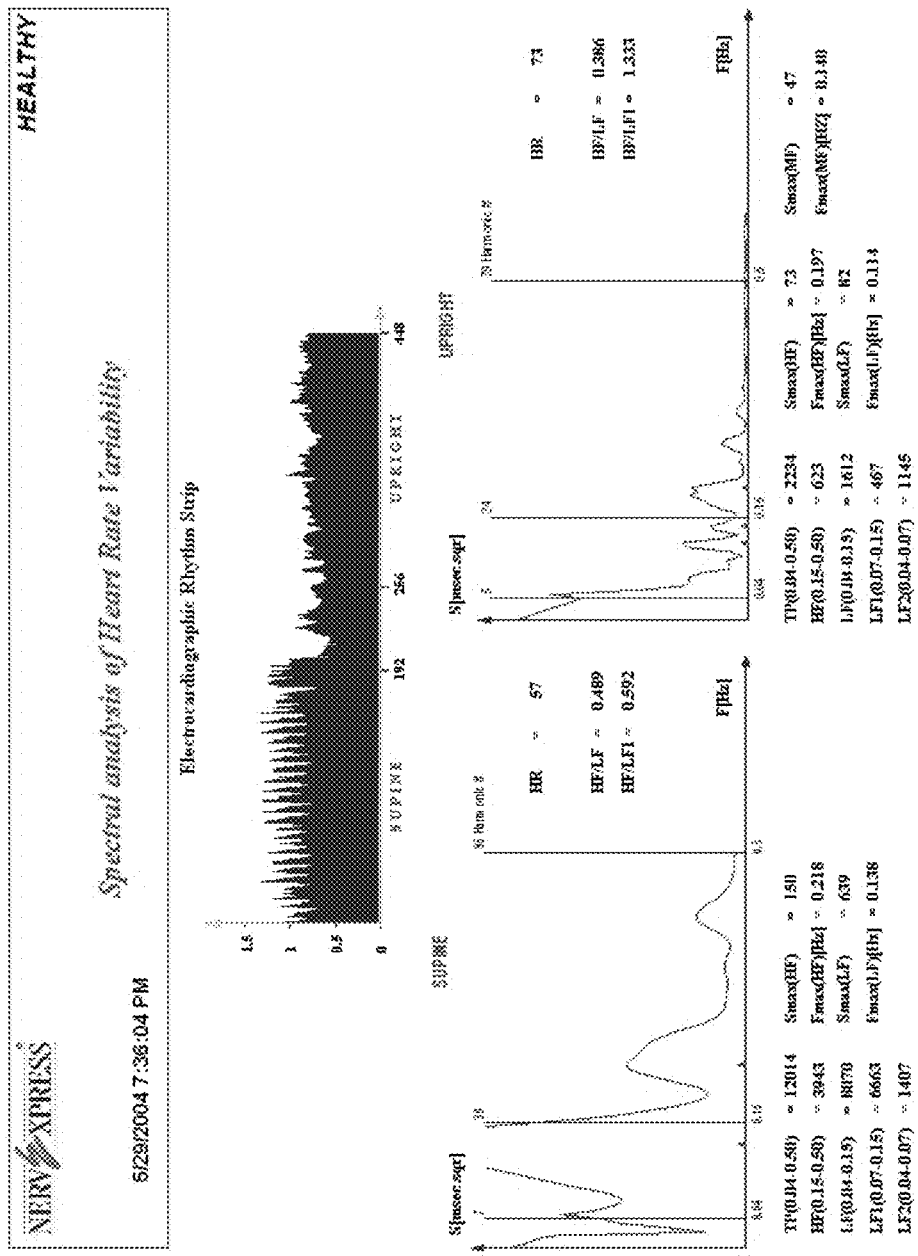
FIGURE 2-A

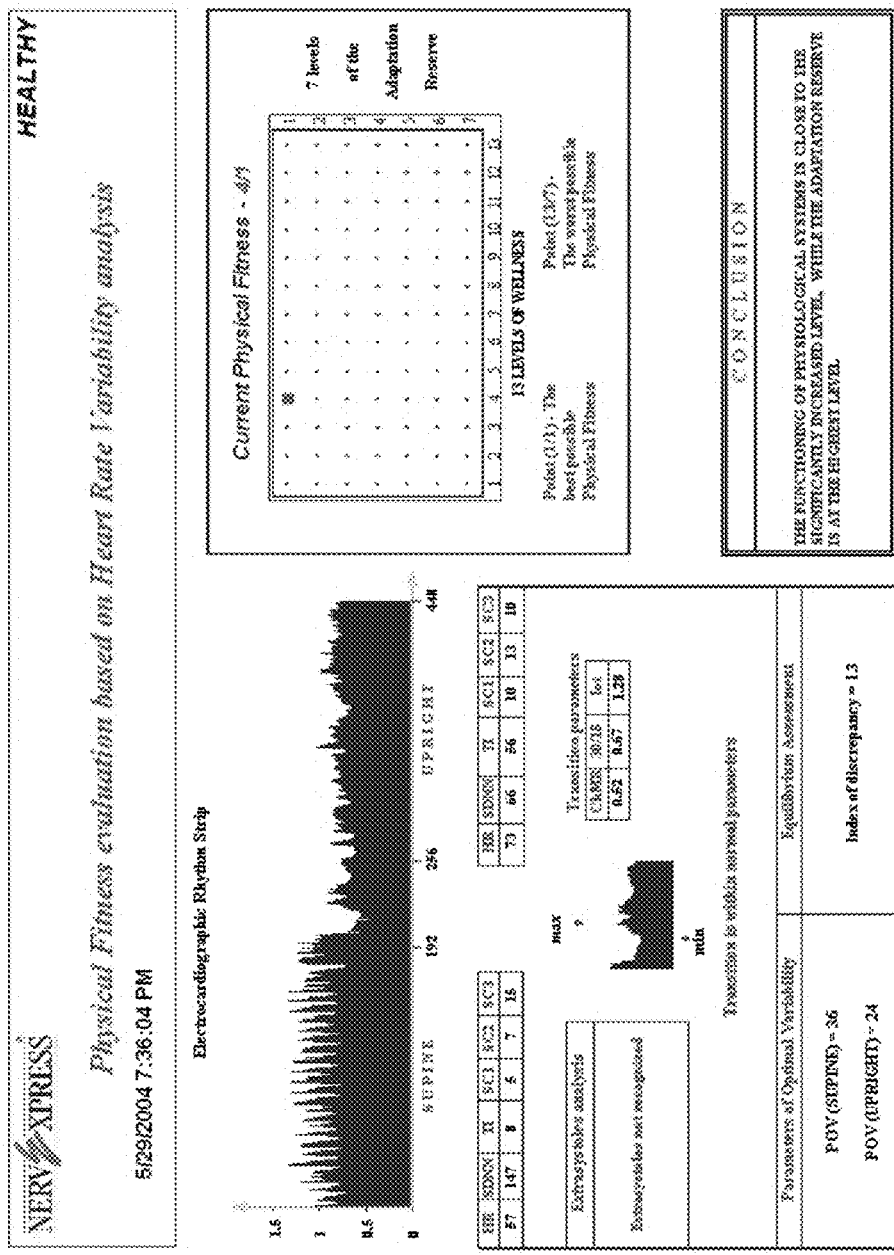
FIGURE 2-B

Areas of Discrepancy from Optimum and Equilibrium functioning
of Heart Rate Variability regulation mechanisms.
(Samples of orthostatic intervention)

Figure 6:
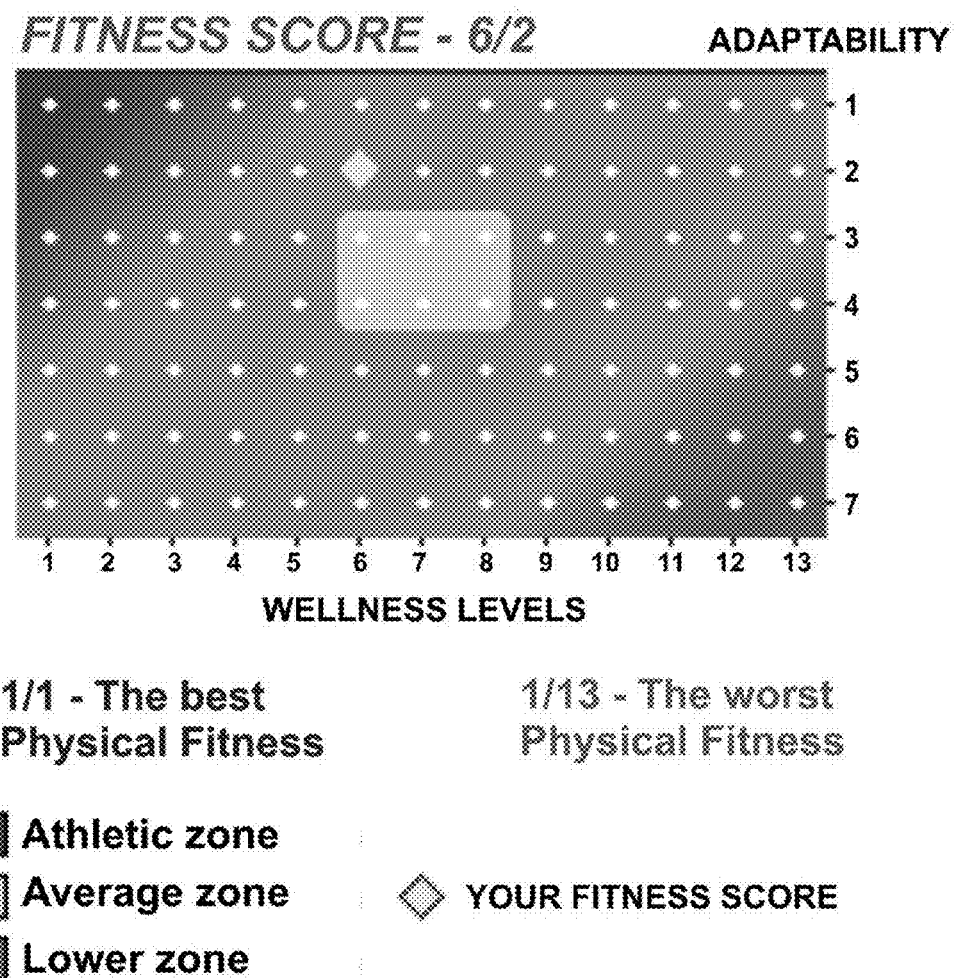

TRANSLATION OF SUBREGIONS ON THE WELLNESS GRAPH
(FROM FIGURE 3) INTO THE X-AXIS VALUES ON THE FITNESS SCORE
GRAPH (FIGURE 6)

| X-AXIS VALUES ON THE FITNESS SCORE GRAPH | SUBREGIONS ON THE WELLNESS GRAPH |
|---|---|
| 1 | 1.0 |
| 2 | 1.1 |
| 3 | 3.1.1, 3.1.2, 2.1.1 |
| 4 | 3.2.1, 3.1.3, 2.2.1 |
| 5 | 3.2.2, 3.1.4, 2.1.2 |
| 6 | 3.2.3, 2.2.2, 2.1.3, 3.1.6 |
| 7 | 3.2.4, 3.1.5, 2.2.3, 3.2.6, 4.6 |
| 8 | 3.2.5, 4.1, 4.5 |
| 9 | 4.2, 4.3, 4.4, 5.6 |
| 10 | 5.4, 5.5 |
| 11 | 5.3 |
| 12 | 5.2 |
| 13 | 5.1 |

FIGURE 4

Schematic representation of how we break down the transition period into two phases

Standard presentation on a hand-held device

US 8,682,421 B2

FITNESS SCORE ASSESSMENT BASED ON HEART RATE VARIABILITY ANALYSIS DURING ORTHOSTATIC INTERVENTION

DESCRIPTION OF THE INVENTION

This invention relates to fitness monitors and the like. This invention is more particularly directed to a device and a method for facilitating quantitative evaluation of level of physical fitness (fitness score) including a PC or handheld, or watch type electronic device having input and output means based on formulas for calculating level of physical fitness through heart rate variability analysis during orthostatic intervention by assessing two main parameters, such as level of adaptation reserve and wellness level.

Figure 1:

Please refer to the FIG. 1 that demonstrates a sample of a handheld device with R-wave generating and transmitting device (any heart rate monitor produced by Polar or any other company) with the results of our method and software calculations displayed on the screen.

I. BACKGROUND OF THE INVENTION

1. Field of the Invention

The field of present invention relates to fitness application and more particularly to a system and a method for facilitating personal physical fitness diagnostic evaluation based on heart rate variability analysis during orthostatic intervention.

2. Description of the Prior Art

The ability of the human organism to withstand physical strain is one of the most important characteristics of health. We can easily distinguish a person who is able to run 10 miles from an individual that cannot even walk 100 yards without a break. The difference between them is in their physical fitness. What is "physical fitness"? According to physiology, it is the ability of the cardio vascular system to provide the function of the organism in the state of heightened strain. Therefore, in assessing the state of the cardio vascular system we are also assessing the state of physical fitness. In recent times, for this purpose, the method of analyzing heart rate variability during the orthostatic challenge test became widely used.

It is well known that orthostatic challenge test is one of the most informative methods used to detect subtle changes in cardiovascular function and specifically its regulatory mechanisms. When body's position is changed from supine to standing, specific changes in heart rate and blood pressure happen as a compensatory reaction of the body. This standup maneuver does not cause any significant physical exertion to a healthy individual. However, if body's regulatory mechanisms do not have adequate functional capacity or there is subtle cardiovascular deficiency then this maneuver can show regulation mechanism dysfunction.

With the help of heart rate variability analysis, it is possible to assess these regulatory mechanism dysfunction. Multiple research studies have shown that reaction of the cardiovascular system on changing body posture and speed of its compensation depends on fitness level. The most indicative parameter of this Heart Rate Variability test is a pattern of heart rate changes caused by a standup maneuver. The weaker and slower this reaction is the less an organism is fit and susceptible to physical exertions, which means lower level of fitness.

Modern techniques of HRV (Heart Rate Variability) analysis allow us to determine an almost exact cardiovascular function condition during the orthostatic challenge test. For example, the Heart Rhythm Scanner program, developed by Biocom Technologies, includes Cardiovascular Health Test. It makes an assessment of the cardiovascular function condition based on two variables:

Cardiovascular Tolerance—indicates dynamic regulatory reserve of the cardiovascular system responsible for a quick reaction to rapid changes in the body's condition.

Cardiovascular Adaptation—indicates the ability of the cardiovascular system to adapt to physiological changes in the body and establish a new stable regulatory state.

The higher the variables of these results the better the ability of the organism to withstand physical strain and as a result a higher level of fitness.

Heart Rate Variability (HRV) is a powerful, very accurate, reliable, reproducible, yet simple method of fitness assessment. Regardless of the vast amount of research in this field, its use by fitness specialists has not yet spread to reach full potential. However, the use of this method will give an individual the ability to customize his physical strain according to cardiovascular function. This will help to avoid overstrain of the organism during workout.

It has been previously proposed to construct fitness monitors to count the number of strides when individual is running. From this, the fitness monitor calculates the distance run by multiplying the number of steps times the individual's stride length. The number of calories consumed by the individual is automatically estimated using the elapsed exercise time and individual is average speed.

Recently, the capacity of the individual's cardiovascular system to bring oxygen to the body tissues has been determined to be the most meaningful index of fitness level. This fitness index is usually expressed in terms of the volume of oxygen taken up by the cardiovascular system, per kilogram of body weight, per minute, this fitness index is commonly referred to as the maximum oxygen intake, or $VO_{2max}$. Generally, this fitness index is higher, the greater the level of fitness is for a given individual. The application of maximal oxygen uptake $VO_{2max}$ as an index of fitness is discussed, e.g., in Astrand and others, for example, in the Journal of Physiology, November 1963. Portable heart rate monitors based on measurement of this index came into existence back in 1982 when Polar launched the first wireless wearable heart rate monitor.

All the fitness evaluation inventions that are based on approximate assessment $VO_{2max}$ have multiple drawbacks. First, all these methods are based on only one fitness parameter (maximal oxygen uptake level) and they require the individual to go through a strict training protocol in order to provide the assessment. Second, these methods require special skills for performing assessment and therefore, usually performed with assistance of the exercise physiologist. In addition, such methods take substantial time to complete, not very precise, difficult to quantify, require to input multiple parameters. Thus, despite the existing methods for fitness evaluation based on Heart Rate Variability Analysis, there is a need for a quick, quantifiable and comprehensive method of fitness assessment, which can be easy performed without supervision and other complications.

* Based on our previous study's result, invented method of Fitness Score assessment well correlated with $VO_{2max}$ approach.

II. SUMMARY OF THE INVENTION

The present invention is directed to a system and a method for facilitating personal physical fitness diagnostic evaluation based on heart rate variability analysis during orthostatic intervention by assessing level of adaptation reserve and wellness level. This evaluation is evolving around method and device in which fitness score is a point on a two-coordinate system presented on a device monitor. X-axis reflects wellness level and y-axis reflects level of adaptation reserve, where:

Wellness level is determined by the effectiveness of the reaction of the regulatory mechanisms, primarily parasympathetic and sympathetic mechanism, to the orthostatic intervention;

* by regulatory mechanisms, we mean parasympathetic regulation, sympathetic regulation, baroreceptors regulation, neuro-humoral regulation, thermo regulation, hormonal and other types of regulations.

Adaptation reserve means the level of adaptability of the myocardium and compensatory ability of the peripheral vascular system during orthostatic intervention.

Calculation of the wellness level is based on the ability of all regulatory mechanisms to function at the optimal, self-maintaining and equilibrium mode during orthostatic intervention. There is a need to note that the best regulatory mechanism is present under condition of Parasympathetic dominancy.

Calculation of the adaptation reserve level is based on the analysis of the transition period between supine and upright position. During the standup maneuver, there is a two-phase transition process between supine and upright position: $1^{st}$ phase is characterized by chronotropic myocardial reaction or adaptability of the myocardium, $2^{nd}$ phase is related to the vascular compensation response from peripheral vascular system.

Our method identifies 13 levels of wellness and 7 levels of the adaptation reserve, all presented as coordinates on a point coordinate system. Each point on a coordinate system is represented simultaneously by two parameters, one being the level of wellness, and another being the level of adaptation reserve.

In the preferred embodiment, the present invention provides automatic calculation of two predetermined factors relevant to an individual's fitness evaluation and produces results in a printable color format by providing hard copy to the individual.

Input of data related to two parameter is performed by the ECG based or Pulse-wave measuring device, which wirelessly transmits R-R intervals or beat-to-beat data during fitness evaluation and testing to the PC, hand-held, or watch type microcomputer device. Such microcomputer device is used to store and analyze collected data.

To summarize, the purpose of the present invention is to provide a method for automatic calculation of two predetermined related to fitness evaluation parameters. Testing is performed with the help of a PC, handheld or watch type device having a software program with relevant for individual evaluation of fitness level and testing; ECG device or Pulse-wave device collecting relevant data to be evaluated; the microcomputer automatically calculating two select parameters; and the microcomputer outputting the result of calculation in a readable and understandable for user format.

III. BRIEF DESCRIPTION OF THE FIGURES

FIG. 1. Sample of a handheld device with illustration on a graph of the fitness score test results demonstrated along with R-wave generating and transmitting device with Bluetooth connection.

FIG. 2. Illustration of method of optimum and non-optimum function of heart rate variability regulation mechanisms during some physical or physiological intervention FIG. 2(A). Showing an example of rhythmografic strip and spectral function during orthostatic intervention corresponding with high level of Optimum variability and middle level of discrepancy from Equilibrium.

FIG. 2(B). Showing the final test result from FIG. 2(A) with calculation of optimum and equilibrium numbers.

Figure 3:
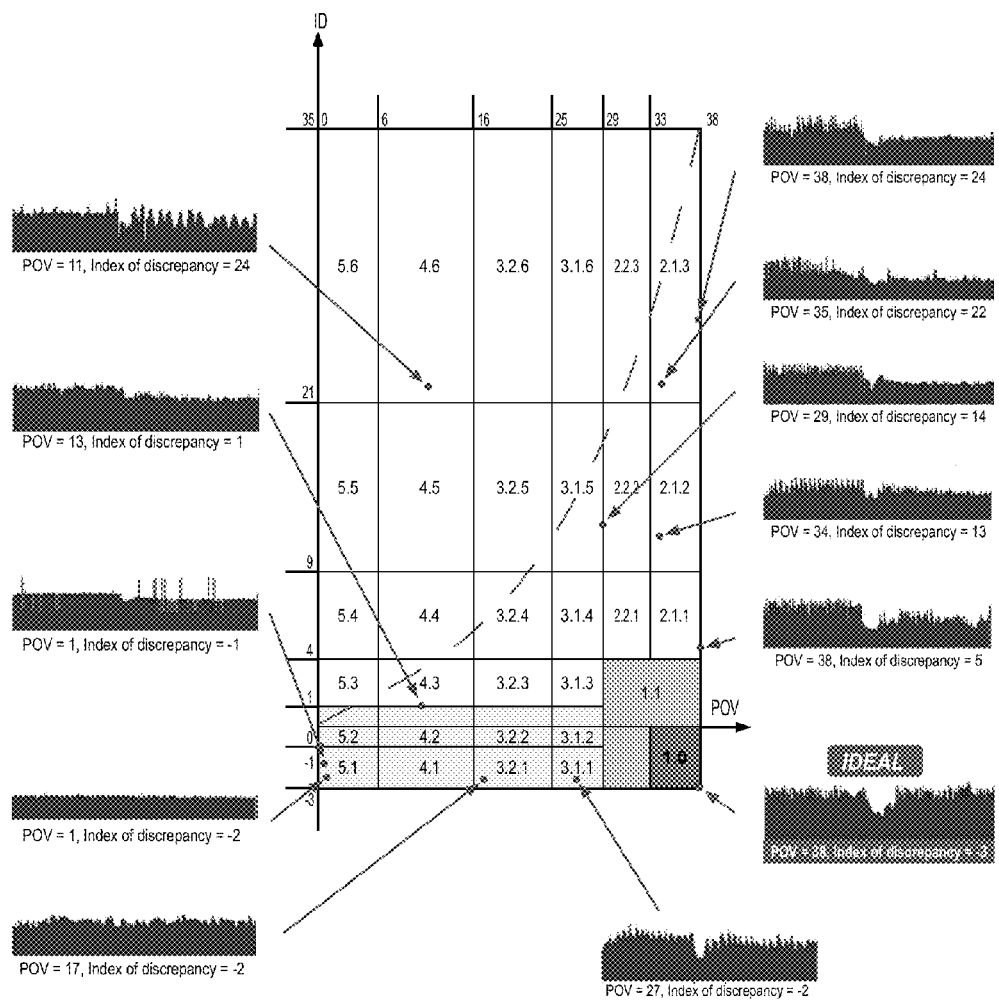

FIG. 3. Graph showing areas of discrepancy from optimum and equilibrium functioning of heart rate variability regulation mechanisms (samples of orthostatic interventions).

FIG. 4. Translation of subregions on the wellness graph (FIG. 3) into the x-axis values on the fitness score graph (FIG. 6).

Figure 5:
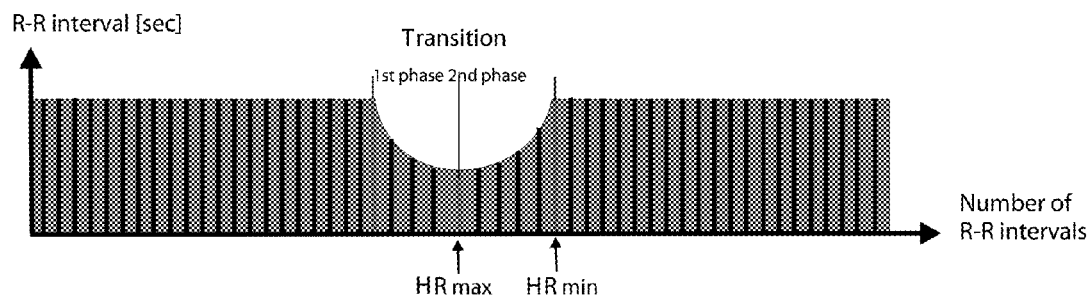

FIG. 5. Schematic representation of how our method breaks down transition period into two phases: $1^{st}$ phase—chronotropic reaction of the myocardium and $2^{nd}$ phase—compensation response from peripheral vascular system.

FIG. 6. Standard presentation of the fitness score test result on a hand held device.

Figure 7:
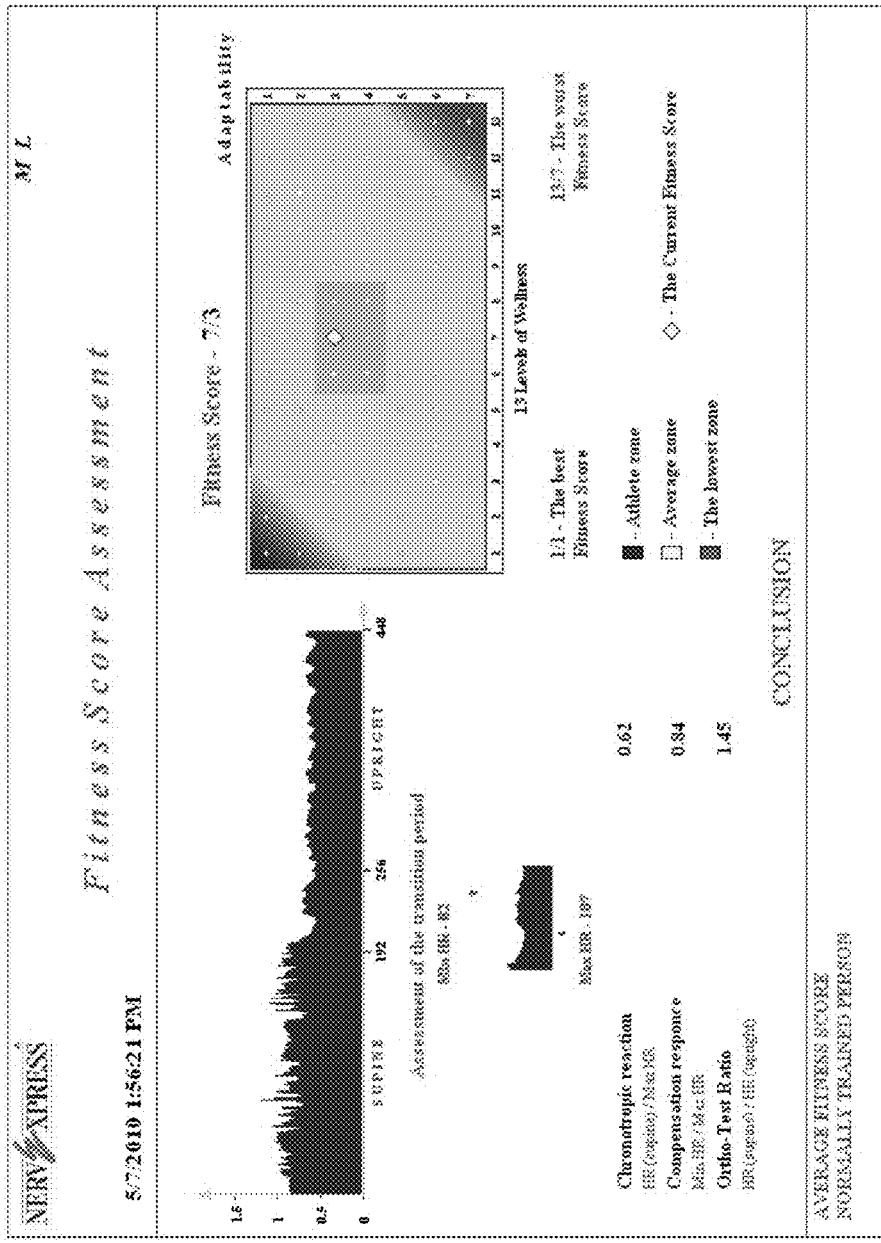

FIG. 7. Standard presentation of the fitness score test result on a typical computer featuring additional information describing analysis of the transition period with appropriate parameters.

IV. DETAILED DESCRIPTION OF THE INVENTION

Method for Assessment of Fitness Score by Determining Wellness Level and Level of Adaptation Reserve Our method comprises of two distinctly separate stages: first, we assess the wellness level, which in essence is assessment of the effectiveness of the body's regulatory mechanisms; second, we assess the level of adaptation reserve. Then we combine these two parameters in order to determine the fitness score result. Let us start with the description of the first stage.

1. Assessment of Wellness Level or Effectiveness of the Body's Regulatory Mechanisms During Orthostatic Intervention In the present method, we propose to use spectral analysis of the heart rate variability and specifically three ranges of spectral function as follow:

| Ranges of Spectral function | | Frequency Range |
|---|---|---|
| *High frequency range-IA | | HF (0.15-0.50 Hz) |
| **Low frequency range | Subdiapason 1-$I_{C1}$ | LF1 (0.07-0.15 Hz) |
| | Subdiapason 2-$I_{C2}$ | LF2 (0.04-0.07 Hz) |

*High frequency range corresponds with parasympathetic regulatory mechanism only.
**Low frequency range related to mixed regulatory mechanisms: sympathetic, parasympathetic, baroreceptors, neuro-humoral, thermo, hormonal and others.
IA-index of activity of the High frequency range,
$I_{C1}$-index of activity of Subdiapason 1 of Low frequency range
$I_{C2}$-is the index of activity of Subdiapason 2 of Low frequency range Based on the experimental analysis of 7,000 volunteers, we identified the maximum power of the spectral function of each frequency range. Such power (measured in msec square) was broken down into 15 levels where is 1 being the highest power and 15 the lowest. Such approach allows to assess the levels of Heart Rate Variability (HRV) control quantitatively by calculating 3 values of indices $I_A$, $I_{C1}$, and $I_{C2}$, and, in addition, to perform qualitative assessment of the status of HRV control by assessing different combinations of activity of HRV regulatory mechanisms. On a stationary stage, HRV regulatory mechanism can be described through these three parameters. Since every index has 15 values, the total number of states of the HRV control is equal to the number of combinations of 3 parameters each multiplied by 15, i.e. 3375 distinct statuses of HRV regulatory mechanisms.

Our goal is to evaluate how HRV regulatory mechanisms function in case of intervention that triggers a specific response of the body's physiological system. Hereinafter, we use intervention as a general term that includes any kind of physical activity, psycho-emotional stress, change of environment (e.g. exposure to heat), medications, and other kinds of impact. For evaluation of functioning of HRV regulatory systems during orthostatic intervention, it is necessary to analyze how they function before and after the intervention. For this analysis, we recommend applying principle of the optimum and the equilibrium status.

The Principles of OPTIMUM and EQUILIBRIUM Status as a Universal Approach to Assessment of Effectiveness of Regulatory Mechanisms During any Intervention The principle of the optimum and equilibrium status are introduced in order to quantitatively evaluate body response to intervention, and, ultimately, to assess the functional status of HRV regulatory mechanisms. The functioning of HRV regulatory mechanisms during intervention is determined by comparing HRV control before and after the impact. For assessment of HRV control before and after the intervention it is necessary to collect some data while the individual is not changing activities and no intervention is performed—such periods are further referred to stationary periods. Thus, the typical simplified testing model includes three stages:

1. Stationary period of rest before intervention;
2. Intervention;
3. Stationary period of rest after intervention.

Substage 1—Determining the Optimum Condition on a Stationary Stage

By analyzing 7,000 cases, we selected 74 clinically healthy individuals with the best possible test results, and found that their three parameters of HRV spectral function satisfy the following conditions:

$$\begin{cases} I_A < I_{C1} < I_{C2} \\ I_A \leq 6 \\ I_{C1} \leq 8 \\ I_{C1} - I_A = \{2, 3\} \\ I_{C2} = \{9/12\} \end{cases}$$

We identified such condition to be the optimum status of regulatory mechanisms on a stationary stage.

Substage 2—Determining the Equilibrium Condition after any Intervention

Equilibrium status of the HRV regulatory mechanisms after intervention is the state when the values of activity indices of $I_A$, $I_{C1}$ and $I_{C2}$ of the stationary stage before the impact are equal to or differ by no more than 3 values from the values on activity indices of the stationary period after the impact.

Thus, the parameters for equilibrium status of HRV control after impact is as follows:

$$\begin{cases} |I_{A\ before\ int} - I_{A\ after\ int}| \leq 1 \\ |I_{C1\ before\ int} - I_{C1\ after\ int}| \leq 1 \\ |I_{C2\ before\ int} - I_{C2\ after\ int}| \leq 1 \end{cases}$$

$I_{A\ before\ int}$ is the value of the index of HRV control by the High frequency range on the stationary period before intervention;

Intervention is any kind of impact including physical activity, such as orthostatic test described below or controlled exercise, medications, psycho-emotional stress and other activities or effects that trigger a reaction of the Autonomic Nervous system and all other regulation mechanisms and can affect HRV;

$I_{A\ after\ int}$ is the value of the index of HRV control by the High frequency range on the stationary period after intervention;

$I_{C1\ before\ int}$ and $I_{C1\ after\ int}$ are the values of the index of HRV control by the Subdiapason 1 of the Low Frequency range on spectral function on the stationary period before and after intervention;

$I_{C2\ before\ int}$ and $I_{C2\ after\ int}$ are the values of the index of HRV control by the Subdiapason 2 of the Low Frequency range on spectral function on the stationary period before and after intervention.

FIG. 2(A) showing an example of rhythmografic strip and spectral function during orthostatic intervention corresponding with high level of Optimum variability and middle level of discrepancy from Equilibrium.

Substage 3—Calculating Discrepancy Between Actual Condition and the Optimum and Equilibrium (Ideal) Condition.

For quantitative assessment of the degree of discrepancy of the actual status to the optimum and equilibrium condition of the regulatory mechanisms, we introduce biparametric index of correlation (B).

The index of correlation is composed of two components:

B1 component evaluates deviation of HRV regulatory mechanisms during impact from the equilibrium state, while B2 component evaluates deviation of HRV regulatory mechanisms from the optimal status on a stationary stage before intervention.

Formulas for calculation of these B components can be written as follows:

$$B1 = (|I_{A\ before\ int} - I_{A\ after\ int}| + |I_{C1\ before\ int} - I_{C1\ after\ int}| + |I_{C2\ before\ int} - I_{C2\ after\ int}|) - 3$$

* The domain of values of B1 will be equal to (−3, 35). B1 is ≤0 when the functioning of HR regulation is at equilibrium.

$$B2 = K_A - Kc_{1.1} - Kc_{1.2} - Kc_2,\ \text{where}$$

$$K_A = \begin{cases} 40 - I_{A\ before\ int} & \text{if } I_{C1} - I_A \neq (0\ \text{to}\ 3)\ \text{and}\ I_A \geq 7 \\ 36 - I_{A\ before\ int} & \text{if } I_{C1} - I_A = (0\ \text{to}\ 3)\ \text{and}\ I_A = 7\ \text{to}\ 9 \\ 33 - I_{A\ before\ int} & \text{if } I_{C1} - I_A = (0\ \text{to}\ 3)\ \text{and}\ I_A > 9 \end{cases}$$

$$K_{C1.1} = \begin{cases} I_{C1} - (I_A + 3) & \text{if } (I_{C1} - I_A) > 3 \\ 2 - (I_{C1} - I_A) & \text{if } (I_{C1} - I_A) \leq 1 \\ 0 & \text{if } (I_{C1} - I_A) = 2, 3 \end{cases}$$

$$K_{C1.2} = \begin{cases} 0 & \text{if } I_{C1} \leq 8 \\ I_{C1} - 8 & \text{if } I_{C1} > 8 \end{cases}$$

$$K_{C2} = \begin{cases} 2 \times (9 - I_{C2}) & \text{if } I_{C2} < 9 \\ I_{C2} - 12 & \text{if } I_{C2} > 1 \\ 0 & \text{if } I_{C2} = 9\ \text{to}\ 12 \end{cases}$$

* The range of values when status of HRV regulatory mechanism is optimal is B2=(33-38).
* The full range of values of B2 is (0-38).

As result of such of calculation we can observe different conditions of the regulatory mechanisms during intervention and distinguish between the areas of optimum and equilibrium as shown on FIG. 3. FIG. 2(B) showing the final test result related to FIG. 2(A) with calculation of optimum and equilibrium numbers.

The position of a point with coordinates B1 and B2 on this graph (FIG. 3) will fall in a certain region and will reflect the degree of discrepancy of the analyzed case of the HRV regulatory mechanism with the optimal and equilibrium condition.

Our method distinguishes 32 subregions for orthostatic intervention as shown on FIG. 3.

In addition, FIG. 3 contains examples of the rhythmographic strips of the most typical statuses of the HRV regulatory mechanisms during orthostatic intervention.

For analysis first, we look at the x-axis for evaluation of the optimum level of regulatory mechanisms on a stage before intervention. The bigger the value of the x-axis, the more optimum the level of regulatory mechanisms is. The smaller the value, the less optimum the level of the regulatory mechanisms. The best optimum level is usually identified in healthy people who regularly exercise and have a great genetic ability.

Then we look at the y-axis to identify the equilibrium level of regulatory mechanisms. The bigger the value, the less equilibrium level meaning that there is a high level of discrepancy of regulatory mechanism.

After this, we look at the two parameters in combination. Based on 7,000 evaluated cases, we have identified the common features characterizing each region on the graph. Cases with the most effective regulatory mechanism will fall under the lower right region on the graph.

Suggested approach based on method of Optimum and Equilibrium can be used for any type of intervention. With different types of intervention there will be assessment of different physiological parameters which depend on the type of utilized intervention. It is necessary to note that for different interventions there will be different subdivision of the regions on the FIG. 3 and correspondingly completely different translation of these subregions into new physiological parameter, for instance tolerance level or physical reserve level instead of wellness level. Such parameter will be chosen based on the type of intervention used in a particular method.

In this case we used this approach only for the assessment of the wellness level during orthostatic Intervention. This is physiological approach, but we find also that some of subregions related with specific pathology. For instance, we find high correlation of subregions 2.1.1, 2.1.2, 2.1.3, 2.2.1, 2.2.2, 2.2.3, 3.1.4, 3.1.5, and 3.1.6 with gastrointestinal system problems and brain deregulation. Subregions 3.2.5, 3.2.6, 4.4, 4.5, 4.6, 5.4, 5.5, and 5.6 are highly correlated with individual psycho-emotional condition such as introversion.

Generally, from physiology point of view, we can translate numbers of subregions into the wellness level based on deviation of each subregions from Optimum and Equilibrium.

FIG. 4 explains translation of subregions from the FIG. 3 into 13 levels of wellness demonstrated on FIG. 6, which shows the graphical result user obtains with the help of our method and software.

Let us now discuss the process of assessment of the level of adaptation reserve.

2. Method for Assessment of the Level of Adaptation Reserve

After we have described the first stage in our method, let us continue with the description of the assessment of the level of adaptation reserve.

Adaptation reserve means level of adaptability of the myocardium and compensatory ability of the peripheral vascular system during orthostatic intervention. Calculations of the adaptation reserve are based on the analysis of the transition period between supine and upright position.

During the standup maneuver, there is a two-phase transition process between supine and upright position:

$1^{st}$ phase characterized by chronotropic myocardial reaction or adaptability of the myocardium, which allows assessing heart functionality and its level of adaptability during intervention;

$2^{nd}$ phase related to the vascular compensation response from peripheral vascular system and allows assessing peripheral vascular tonus and its regulatory mechanisms.

FIG. 5 demonstrates schematic representation of how we break down transition period into two phases.

Quantitative assessment of the $1^{st}$ and $2^{nd}$ phases is conducted based on the rhythmographic analysis performed during orthostatic intervention. The following parameters are analyzed:

C 1—coefficient of the $1^{st}$ phase, which can be calculated as follows:

$$C1 = \frac{R\min}{R_{1average}}$$
$$= \frac{\text{min value of } R\text{-}R \text{ interval during transition period}}{\text{average } R\text{-}R \text{ interval on a first stationary stage (before intervention)}}$$

C 2—coefficient of the $2^{nd}$ phase, which can be calculated as follows:

$$C2 = \frac{R\min}{R\max}$$
$$= \frac{\text{min value of } R\text{-}R \text{ interval during transition period}}{\text{max value of } R\text{-}R \text{ interval during transition period}}$$

$I_{ot}$—index of the orthotest, which reflects overall reaction of the heart rate during orthotest, calculated as follows:

$$I_{ot} = \frac{R_{1average}}{R_{2average}}$$
$$= \frac{\text{average } R\text{-}R \text{ interval on a first stationary stage (before intervention)}}{\text{average } R\text{-}R \text{ interval on a second stationary stage (after intervention)}}$$

Rhythmographic analysis performed during orthostatic intervention allowed us to distinguish five specific types of transition processes:

1. Normal or conditionally normal transition process
   1.1 normal
   1.2 conditionally normal
2. Generally weakened reaction of both phases of the transition period (by at least 4 values)
   2.1 slight decrease
   2.2 moderate decrease
   2.3 significant decrease
   2.4 sharp decrease
3. Weakened $2^{nd}$ phase with normal or conditionally normal $1^{st}$ phase (by at least 4 values)
   3.1 moderate decrease 3.2 significant decrease
3.3 sharp decrease
3.4 $2^{nd}$ phase is absent 4. Weakened $1^{st}$ phase with inexistence of the $2^{nd}$ phase (by at most 3 values)
   4.1 moderate decrease
   4.2 significant decrease
   4.3 sharp decrease 5. Mixed reaction to orthostatic intervention—various mixes of weakened reactions on a $1^{st}$ And $2^{nd}$ phases (by at most 3 values)
   5.1 moderate decrease of the $1^{st}$ phase with the significant decrease of the $2^{nd}$ phase
   5.2 significant decrease of the $1^{st}$ phase with the sharp decrease of the $2^{nd}$ phase
   5.3 moderate decrease of the $1^{st}$ phase with the sharp decrease of the $2^{nd}$ phase These 5 groups of transition processes are determined by 27 conditions of the next 4 parameters:
C1, C2, Iot and C1-C2 as shown below (please note that these values are decimal values, but for simplicity of presentation we have multiplied each value by 100):

| CONDITION NUMBER | C1 | C2 | Iot | C1-C2 | SUBGROUP NUMBER |
|---|---|---|---|---|---|
| 1 | (39, 58), | (39, 63), | (90, 129), | (−4, 23) | 1.1 |
| 2 | (39, 59), | (39, 59), | (90, 107), | (−4, 20) | 1.1 |
| 3 | (59, 63), | (56, 68), | (90, 125), | (−4, 10) | 1.2 |
| 4 | (59, 63), | (59, 72), | (90, 119), | (−4, 10) | 1.2 |
| 5 | (64, 68), | (65, 72), | (90, 119), | (−4, 6) | 2.1 |
| 6 | (69, 72), | (69, 73), | (90, 119), | (−4, 4) | 2.1 |
| 7 | (73, 75), | (71, 76), | (90, 119), | (−4, 4) | 2.2 |
| 8 | (73, 77), | (71, 77), | (90, 116), | (−4, 4) | 2.2 |
| 9 | (78, 85), | (78, 87), | (90, 112), | (−4, 10) | 2.3 |
| 10 | (86, 90), | (86, 90), | (90, 109), | (−4, 4) | 2.4 |
| 11 | (39, 59), | (63, 70), | (115, 124), | (−4, 34) | 3.1 |
| 12 | (60, 63), | (63, 70), | (105, 124), | (−4, 14) | 3.1 |
| 13 | (39, 59), | (71, 77), | (125, 145), | (12, 40) | 3.2 |
| 14 | (60, 63), | (71, 77), | (118, 145), | (8, 19) | 3.2 |
| 15 | (39, 59), | (74, 82), | (134, 145), | (19, 40) | 3.3 |
| 16 | (60, 63), | (74, 82), | (124, 145), | (15, 24) | 3.3 |
| 17 | (39, 59), | (83, 101), | (146, 180), | (14, 70) | 3.4 |
| 18 | (60, 63), | (83, 100), | (136, 180), | (20, 50) | 4.4 |
| 19 | (69, 76), | (84, 100), | (110, 145), | (10, 31) | 4.1 |
| 20 | (77, 83), | (86, 100), | (110, 130), | (9, 23) | 4.2 |
| 21 | (84, 88), | (86, 111), | (104, 120), | (−2, 27) | 4.3 |
| 22 | (70, 76), | (77, 83), | (107, 130), | (7, 19) | 5.1 |
| 23 | (77, 83), | (83, 100), | (110, 121), | (6, 23) | 5.1 |
| 24 | (71, 76), | (85, 100), | (126, 166), | (13, 29) | 5.2 |
| 25 | (64, 68), | (70, 79), | (102, 142), | (2, 16) | 5.2 |
| 26 | (64, 68), | (78, 88), | (102, 146), | (8, 28) | 5.3 |
| 27 | (64, 68), | (86, 100), | (102, 150), | (12, 34) | 5.3 |

These 27 conditions of transition processes are translated into 7 levels of adaptation reserve as shown below:

| LEVEL # | CONDITION NUMBER |
|---|---|
| LEVEL 1: | 1, 8, 11, 14, 17 |
| LEVEL 2: | 2, 9, 12, 15, 18 |
| LEVEL 3: | 3, 10, 13, 16, 19 |
| LEVEL 4: | 4, 26, 27 |
| LEVEL 5: | 5, 20, 23, 25 |
| LEVEL 6: | 6, 21, 24 |
| LEVEL 7: | 7, 22 |

3. Fitness Score Assessment

After all mentioned above steps are performed, we present graphical approach to analysis of the overall fitness score based on two parameters: wellness level and level of adaptation reserve. Please refer to the FIG. 6, which contains graph with 7 levels of adaptation reserve (on y-axis) and 13 wellness levels (on x-axis). The best fitness score is represented by the point (1, 1) on the graph, and the worst fitness score is at the point (13, 7). FIG. 6 is the typical presentation for the handheld device. On FIG. 7, we show Fitness Score presentation provided on a regular computer with more detailed information about transition process.

What is claimed is:

1. A method of assessing a Fitness Score of a person, comprising:
   determining diagnostic indicators of the fitness score using heart rate variability (HRV) analysis of ECG signals during orthostatic intervention by:
   assessing a level of Overall Adaptation Reserve of the person, by analyzing a transition period of the person between a supine position and an upright position during orthostatic intervention;
   determining a diagnostic indicator of adaptability of the myocardium; and
   determining a diagnostic indicator of compensatory ability of the peripheral vascular system.

2. The method of claim 1, further comprising determining the diagnostic indicator of adaptability of the myocardium by calculating a ratio of an R-R interval minimum during the transition period to an average R-R interval at the supine position.

3. The method of claim 1, further comprising determining the diagnostic indicator of compensatory ability of the peripheral vascular system by calculating a ratio of an R-R interval minimum during the transition period to an average R-R interval at the upright position.

4. The method of claim 1, further comprising distinguishing types of transition periods between the supine position and the upright position by dividing 16 combinations of values of the diagnostic indicators of adaptability of the myocardium and compensatory ability of the peripheral vascular system into the following 5 groups of physiological indicators:
   Group 1: normal or conditionally-normal transition period;
   Group 2: general decrease of both the adaptability of the myocardium and the compensatory ability of the peripheral vascular system;
   Group 3: decrease of the compensatory ability of the peripheral vascular system and normal or conditionally normal adaptability of the myocardium;
   Group 4: decrease of the adaptability of the myocardium with absence of the compensatory ability of the peripheral vascular system phase; and
   Group 5: mixed type of decrease of the adaptability of the myocardium and the compensatory ability of the peripheral vascular system orthostatic intervention.

5. The method of claim 4 further comprising translating the 16 combinations of values of the diagnostic indicators of adaptability of the myocardium and compensatory ability of the peripheral vascular system into the following 7 groups of similar Overall Adaptation Reserve levels:
   Level 1—High Adaptation Reserve;
   Level 2—Conditionally High Adaptation Reserve;
   Level 3—Normal Adaptation Reserve;
   Level 4—Conditionally Normal Adaptation Reserve;
   Level 5—Slightly Decreased Adaptation Reserve;
   Level 6—Significantly Decreased Adaptation Reserve; and
   Level 7—Sharply Decreased Adaptation Reserve.

6. A method of assessing a Fitness Score of a person, comprising:
   determining diagnostic indicators of the fitness score using heart rate variability (HRV) analysis of ECG signals during orthostatic intervention by:
   assessing a Wellness Level of the person by determining an Optimum and an Equilibrium status of HRV regulatory mechanisms during any intervention by assessing an Optimum status of HRV regulatory mechanisms when the person is in a stationary period before intervention using spectral analysis of R-R interval variability; and
   calculating a parameter of the Optimum status by calculating a ratio of the Optimum status and an Actual Optimum status that is less than or equal to the Optimum status.

7. The method of of claim 6, further comprising defining the Optimum status as an ideal status of HRV regulatory mechanisms determined as meeting specific conditions of spectral function components.

8. The method of claim 7, further comprising determining the Optimum status by assessing the specific conditions of spectral function components using the following indices:
   Index of High Frequency component (Ia), wherein the Ia is an indicator of parasympathetic activity having a power of sub range (0.15-0.5 Hz);
   Index of Low Frequency 1 component (Ic1), wherein the Ic1 is an indicator of mixed sympathetic-parasympathetic activity and of baroreflex sensitivity having a power of subrange (0.07-0.15 Hz);
   Index of Low Frequency 2 component (Ic2), wherein the Ic2 is an indicator of mostly sympathetic activity having a power of sub range (0.04-0.07 Hz);
   wherein the indices conform to the following conditions:
   a) Ia is less than Ic1 and Ic1 is less than Ic2;
   b) Ia is less than or equal to 6;
   c) Ic1 is less than or equal to 8;
   d) the difference between Ic1 and Ia is equal 2 or 3;
   e) Ic2 is equal to {9-12}.

9. The method of claim 6, further comprising calculating the parameter of Optimum status (B2) by using the following formulae:

$$B2 \text{ [ms.square]} = Ka - Kc1.1 - Kc1.2 - Kc2, \text{ where:}$$

|40−Ia, if Ic1<>{0-3} and Ia≥7
Ka=|36−Ia, if Ic1−Ia={0-3} and Ia={7-9}
|33−Ia, if Ic1−Ia={0-3} and Ia>9;
|Ic1−(Ia+3), if (Ic1−Ia)>3
Kc1.1=|2−(Ic1−Ia), if (Ic1−Ia)<=1
|0, if (Ic1−Ia)={2, 3};
|0, if Ic1<=8
Kc1.2=|Ic1−8, if Ic1>8;
|2×(9×Ic2), if Ic2<9
Kc2=|Ic2−12, if Ic2>1
|0, if Ic2={9-12}.

10. A method of assessing a Fitness Score of a person, comprising:
   determining diagnostic indicators of the fitness score using heart rate variability (HRV) analysis of ECG signals during orthostatic intervention by:
   assessing a Wellness Level of the person by determining an Optimum and an Equilibrium status of HRV regulatory mechanisms during any intervention by defining the Equilibrium status as a condition where HRV regulatory mechanism recover to a pre-intervention status and by using the following parameters for assessing the Equilibrium status of HRV regulatory mechanisms:
   a) Ia (before intervention)−Ia (after intervention)≤1;
   b) Ic1 (before intervention)−Ic1 (after intervention)≤1;
   c) Ic2 (before intervention)−Ic2 (after intervention)≤1.

11. The method of claim 10, further comprising calculating a parameter of deviation of HRV regulatory mechanisms from Equilibrium status (B1) as follows:

$$B1 = ((Ia(\text{before intervention}) - Ia(\text{after intervention})) + (Ic1(\text{before intervention}) - Ic1(\text{after intervention})) + (Ic2(\text{before intervention}) - Ic2(\text{after intervention}))) - 3.$$

12. A method of assessing a Fitness Score of a person, comprising:
   determining diagnostic indicators of the fitness score using heart rate variability (HRV) analysis of ECG signals during orthostatic intervention by:
   determining an Optimum and an Equilibrium status of HRV regulatory mechanisms during any intervention by and representing the Optimum and the Equilibrium status as a point on a graph system having two coordinates, and
   defining where an area of existing Optimum and Equilibrium status on the graph system as follows:
   x-axis represents Optimum status, ranging [0-38];
   y-axis represents Equilibrium status, ranging [−3-35].

13. The method of claim 12, further comprising dividing the area of existing Optimum and Equilibrium status into 32 sub regions of Optimum and Equilibrium status during orthostatic intervention.

14. The method of claim 13, further comprising translating numbers of the 32 sub regions into the following 13 levels of Wellness based on levels of functioning of physiological systems:
   Level 1—High Level;
   Level 2—Conditionally High;
   Level 3—Significantly Above Average;
   Level 4—Moderately Above Average;
   Level 5—Slightly Above Average;
   Level 6—Average;
   Level 7—Average;
   Level 8—Average;
   Level 9—Slightly Below Average;
   Level 10—Moderately Below Average;
   Level 11—Significantly Below Average;
   Level 12—Sharply Below Average;
   Level 13—Sharply Below Average.

15. A method of assessing a Fitness Score of a person, comprising:
   determining diagnostic indicators of the fitness score using heart rate variability (HRV) analysis of ECG signals during orthostatic intervention; and
   graphically representing the Fitness Score as a point on a graph system having
   an x-axis representing 13 levels of Wellness, and
   a y-axis representing 7 levels of adaptation reserve.

* * * * *